(12) United States Patent
Alexander et al.

(10) Patent No.: US 6,541,250 B2
(45) Date of Patent: Apr. 1, 2003

(54) CONTINUOUS ADHERENT MELANOCYTE CELL LINE

(75) Inventors: Jeannine Alexander, Clifton Park, NY (US); William I. Cox, East Greenbush, NY (US)

(73) Assignee: Aventis Pasteur Limited, North York (CA)

(*) Notice: Subject to any disclaimer, the term of this patent is extended or adjusted under 35 U.S.C. 154(b) by 0 days.

(21) Appl. No.: 09/837,011

(22) Filed: Apr. 18, 2001

(65) Prior Publication Data

US 2002/0006662 A1 Jan. 17, 2002

Related U.S. Application Data

(60) Provisional application No. 60/213,613, filed on Jun. 22, 2000.

(51) Int. Cl.[7] .......................... C12N 5/00; C12N 5/02; C12N 1/20; C12N 15/00
(52) U.S. Cl. .................... 435/325; 435/383; 435/252.3; 435/320.1
(58) Field of Search ................. 435/325, 383, 435/252.3, 320.1

(56) References Cited

FOREIGN PATENT DOCUMENTS

WO  WO9806746  2/1998

OTHER PUBLICATIONS

Adema, G. J. et al. "Molecular Characterization of the Melanocyte Lineage–specific Antigen gp100." *The Journal of Biological Chemistry.* vol. 269, No. 31, 1994, pp. 20126–20133.

Zhai, Yifan et al. "Cloning and Characterization of the Genes Encoding the Murine Homologues of the Human Melanoma Antigens MART1 and gp100." *Journal of Immunotherapy.* vol. 20, No. 1, 1997, pp. 15–25.

Bakker, A.B. H. et al. "Identification of a Novel Peptide Derived from the Melanocyte–Specific gp100 Antigens as the Dominant Epitope Recognized by an HLA–A2.1–Restricted Anti–Melanoma CTL Line." *International Journal of Cancer.* vol. 62, No. 1,1995, pp. 97–102.

Kawakami, Y. et al. "Identification of a Human Melanoma Antigen Recognized by Tumor–Infiltrating Lymphocytes Associated with In Vivo Tumor Rejection." *Proceedings of the National Academy of Sciences of USA, National Academy of Science.* vol. 91, No. 14, Jul. 5, 1994, pp. 6458–6462.

Adema, G. J. et al. "PME117 is Recognised by Monoclonal Antibodies NKI–BETEB, HMB–45 ANDHMB–50 and by Anti–Melanoma CTL." *British Journal of Cancer.* vol. 73, No. 9, 1996, pp. 1044–1048.

Shimizu, et al. 1989. Production of Human Cells Expressing Individual Transferred HLA–A,–B,–C Genes Using an HLA–A,–B,–C Null Human Cell Line. J. Immunol. 142:3320–3328.

Robinson, et al., IMGT/HLA Database—a sequence database for the human major histocompatability complex. Tissue Antigens 55:280–287 (1999).

Johnson, et al. 2000. Rapid Cloning of HLA Class I cDNAs by Locus Specific PCR. J. Immunol. Meth. 233:119–129.

Arnett, et al. 1995. HLA Class I Nucleotide Sequences, 1995. Tissue Antigens 45:217–257.

Mason, et al. 1998. HLA Class I Region Sequences, 1998. Tissue Antigen 51:417–466.

*Primary Examiner*—Christina Chan
*Assistant Examiner*—Michail A Belyavskyi

(57) ABSTRACT

The present invention comprises a novel immortal non-adherent human melanocyte cell line, designated WC-1 14.07. This cell line is stable and MHC class I negative. This continuous melanocyte cell line can be used as a source of melanin and hgp100. The Class I MHC-negative nature of this cell line allows it to be used as a target for transfection with MHC class I genes, providing a novel source of hgp100 in a pre-determined MHC context. The cell line can thus be used in a variety of ways, directly or indirectly, in the development and manufacture of vaccines for melanoma.

8 Claims, No Drawings

CONTINUOUS ADHERENT MELANOCYTE CELL LINE

This application claims the benefit of U.S. Provisional Application No. 60/213,613, filed on Jun. 22, 2000.

BACKGROUND OF THE INVENTION

1. Field of the Invention

The present invention relates to the field of melanocyte cell lines.

2. Summary of the Invention

Melanoma is a malignant neoplasm derived from cells capable of forming melanin. Melanoma, together with squamous cell and basal cell carcinoma, comprises skin cancer, the most commonly diagnosed cancer in the U.S. Melanoma represents a serious public health problem. It is the fifth most common cancer in the United States, and is associated with the highest case fatality rate of all skin cancers. (Rigel, D. S. Malignant Melanoma: perspectives in incidence and its effects on awareness, diagnosis and treatment, CA Cancer J. Clin. 1996 46: 195–198; MMWR May 3, 1996 45, #17).

Melanocytes and melanoma cells express melanogenisis-related proteins (Orlow et al. 1995; del Marmol & Beerman, 1996). These proteins contribute to the antigenicity of melanomas, making them attractive targets for cancer vaccines.

Hgp100 is a melanoma-associated glycoprotein antigen that is closely related to the melanogenesis-related protein pmel17. These proteins differ at the genetic level by an in frame deletion of a 21 base pair sequence in hgp100 (Adema et al. 1994). For purposes of this disclosure, gp100 and pmel17 are used interchangeably.

gp100 is an attractive candidate for a cancer vaccine against melanoma. Prototype vaccines based on synthetic gp100 peptides or recombinant viral vectors are currently in phase I clinical trials. Studies on gp100 polypeptide have been hampered by the limited availability of purified native or recombinant protein. It is difficult and impractical to purify hgp100 (human gp100) from melanoma specimens, and such approaches do not yield sufficient material for use in vaccines.

Recombinant technology should provide high quality, highly purified hgp100 in sufficient quantity to be useful in therapeutic cancer vaccines. To date, only one group has reported success in cloning and expressing of hgp100 in vitro. (Huang et al. J. Invest Dermatol.) Huang et al. derived the hgp100 gene from an established melanoma cell line and cloned the gene into E. coli. However, hgp100 is a glycoprotein and prokaryotes are not capable of glycosylating recombinant proteins. Thus, expression of cloned hgp100 in E. coli leads to the production of a recombinant product that differs in significant respects from the native protein. Critical antigenic determinants may be lost, limiting the applicability of such proteins to vaccines. Thus, a need exists for a method of production of high levels of glycosylated hgp100 Ag in a form more closely related to that which exists in nature.

SUMMARY OF THE INVENTION

The present invention provides cells, designated WC-1 14.07 (ATCC accession no. PTA-1275), that can be used as a source of hgp100. Cells of the WC-1 14.07 eukaryotic cell line endogenously express hgp100, and since hgp100 is a known tumor-associated antigen, cells of the WC-1 14.07 cell line are a useful source of hgp100 for use in immunological formulations, e.g., as a vaccine to treat patients with melanoma. Eukaryotic cell line WC-1 14.07 is also a useful source of hgp100 for use as a research reagent for immunologists studying the cell-mediated immune responses to hgp100 and biological processes involving hgp100. The cells can be inactivated and used directly to stimulate the host immune response to hgp100. Alternatively, hgp100 can be extracted and purified from the cells using affinity chromatography (Wilchek, M., Miron, T., and Kohn J. 1984. Affinity Chromatography. Methods Enzymol. 104: 3–55). hgp100 could be used in immunological assays to measure T cell proliferation or antibodies to hgp100.

The cells of the present invention can also be used as a source of melanin. Melanin is produced in melanosomes and is transferred to keratinocytes. It has been shown to reduce the amount of chromosome aberrations when injected directly into cells prior to radiation exposure (Mosse, I, Kostrova L, Subbot S, Maksimenya I, Molophei V.) Melanin decreases clastogenic effects of ionizing radiation in human and mouse somatic cells and modifies the radioadaptive response. Radiat Environ Biophys 2000 Mar; 39(1):47–52). Melanin can also be used for the therapeutic and cosmetic modification of hair. Melanin targeted to hair follicles by topical application results in the restoration of hair pigment (Hoffinan RM. Topical liposome targeting of dyes, melanins, genes and proteins selectively to hair follicles. J Drug Target 1998;5(2):67–74).

The cells of the present invention can also be used as a source of s100. s100 is a multigenic family of $Ca^{2+}$ binding proteins and has 19 different members that are differentially expressed in a large number of cell types. Members of s100 have been implicated in a number of $Ca^{2-}$ dependent activities including protein phosphorylation, enzyme activities, cell proliferation and neoplastic transformation and differentiation, cytoskeleton, membrane organization, inflammation and oxidative cell damage (Donato R. Functional roles of s100 proteins, calcium-binding proteins of the EF-hand type. Biochim Biophys Acta 1999 Jul 8:1450(3):191–231). Altered expression of s100 proteins is associated with several human disorders including cancer, neurodegenerative diseases, cardiomyopathies, inflammations, diabetes and allergies (Heizmann CW, Cox JA. New perspectives on s100 proteins: a multi-functional $Ca(2+)$-, $Zn(2+)$- and $Cu(2+)$-binding protein family. Biometals 1998 Dec;11(4):383–97). Thus, s100 could be prepared from cells of the present invention and used in the research and treatment of these disorders.

Yet another use of the cells of the present invention is as a universal recipient for expression of hgp100 in the context of pre-determined Class I MHC determinants. Since WC-1 14.07 has lost its MHC Class I expression, transfection of this cell line with plasmids encoding any MHC Class I molecule results in expression of cell surface MHC Class I molecules with appropriate hgp100 peptides. These cells, modified by transfection, comprise yet another aspect of the present invention. Such cells can readily be prepared by standard molecular biology methods, see, e.g., Maniatis et al., and be used, for example, as targets for lysis by cytotoxic T-lymphocytes. These transfected cells could eliminate the need for an autologous cell line when monitoring patients for specific hgp100 epitopes. One target cell line could be used for all patients being monitored during a clinical trial.

DETAILED DESCRIPTION OF THE INVENTION

The practice of the present invention will employ, unless otherwise indicated, conventional methods of immunology, molecular biology, cell biology and recombinant DNA techniques known to those skilled in the, art. Such techniques are explained fully in the literature. See, e.g., Sambrook, et al., MOLECULAR CLONING, A LABORATORY MANUAL, Second Ed. (1989); Nucleic Acid Hybridization (B. D. Hames & S. J. Higgins, 1984); Animal Cell Culture (R. Freshney ed. 1986); Immunochemical Methods in Cell and Molecular Biology (Mayer & Walker, eds., Academic press, London, 1987); Protein Purification: Principles and Practice, Second Edition (Scopes, ed., Springer-Verlag, N.Y. 1987); Current Protocols in Immunology (John Wiley & Sons, NY 1998); Antibodies, a Laboratory Manual (Ed Harlow and David Lane, eds, Cold Spring Harbor, N.Y. 1988); and Fundamental Immunology (Paul, ed, Raven Press, NY 1993).

The present invention provides a stable, adherent, continuous melanocyte cell line, designated WC-1 14.07 (ATCC accession no. PTA-1275). The cell line was obtained by culturing the peripheral blood mononuclear cells of an adult male human volunteer under conditions that allowed for the selection of stable adherent cells. The WC-1 14.07 line, expanded from cells selected after 60 days of weekly subculture in standard tissue culture medium, is of melanocyte origin. Characterization of WC-1 14.07 revealed the following phenotype: s100, hgp100 and melanin positive; CD11c, CD80, CD86 negative; weakly CD14+; HLA DR, DQ, DP negative; and MHC Class I/II negative.

The melanocyte cell line of the present invention provides a useful source of hgp100, melanin and s100. The stability and continuous nature of this cell line makes it amenable to large scale culture in tissue culture. Cells are then isolated, disrupted by standard techniques, and constituents of interest purified by standard techniques known to those skilled in the art. For example, immunoaffinity columns are prepared by immobilizing antibody to hgp100 on cyanogen boride-activated Sepharose 4B. Extracts of the melanocyte cell line WC-1 14.07 are then passed over the immunoaffinity column under conditions that allow for antigen-antibody binding. Non-specific cell constituents and debris pass through the immunoaffinity column and are discarded or used for other purposes. The hgp100 is then eluted from the immunoaffinity column by washing with a buffer that disrupts the antigen-antibody bond (e.g., by applying a pH or salt gradient). Similarly, antibodies to melanin and s100 can be used to prepare specific immunoaffinity columns with which to purify melanin or s100 from extracts of WC-1 14.07.

The cells of the present invention can also be modified by transfection to express heterologous proteins, such as, in particular, predetermined MHC constituents. Transfection with a class I histocompatibility gene under conditions favorable to expression of such gene then provides a modified melanocyte cell line that produces hgp100 (or other constituents) in the context of the predetermined MHC molecule. Thus, hgp100 is presented on the surface of such modified cell together with the MUC determinant and will thereby be efficiently presented to T-cells. Standard methods well known to those skilled in the art can be employed to effect transfection.

The invention is further illustrated by the following examples, which are meant to be illustrations only and are not intended to limit the present invention to specific embodiments. All publications cited herein are hereby incorporated by reference in their entirety.

EXAMPLES

Example 1

Derivation of Adherent Melanocyte Cell Lines

Human adherent peripheral blood mononuclear cells (PBMC) were obtained from a normal healthy HLA 0201 donor, using conventional techniques. PBMC were separated by centrifugation in ficoll-Hypaque Plus (Pharnacia, Uppsala, Sweden). The PBMC were cultured for 7 days in growth medium, obtained from Gibco-BRL (Grand Island, N.Y.) supplemented with human Granulocyte monocyte-colony stimulating factor (rhGM-CSF; 800 units/ml) (Peprotech, Rocky Hill, N.J.) and recombinant human Interleukin-4 (rhIL-4; 500 units/ml) (Peprotech, Rocky Hill, N.J.). The growth Medium consisted of RPMI 1640+L-glutamine, 10% fetal bovine serum, an additional 1% L-glutamine, 1% penicillin-streptomycin and 1% 2-β mercaptoethanol.

On or about day 7, loosely adherent potential dendritic cells (DC) were removed. These cells were stained with monoclonal antibodies against known molecules expressed on DCs and include CD11c, CD80, CD86, CD83, CD40 and HLA-DR, -DP, -DQ and quantitated by flow cytometry. Cell populations were typically 80–100% positive for these DC markers. Adherent cells remaining were cultured in the same medium in the presence of GM-CSF, but without rhIL-4. The cells were fed weekly with fresh medium and rhGM-CSF as needed. During the first 7–45 days, growth was minimal. Around day 45, cell growth began to increase and at approximately day 60 an adherent cell population was isolated which grew well, doubling in cell number every 2 days. Cells were subcultured weekly by removal with Trypsin-EDTA and cultured in RPMI 1640+L-glutamine, 10% fetal bovine serum, an additional 1% L-glutamine, 1% penicillin-streptomycin and 1% 2-β mercaptoethanol by adding approximately $2 \times 10^6$ cells in a T75 flask containing 100 cc growth medium. Expansion of cells was done in a T175 flask seeded with $5 \times 10^6$ cells in 40 cc of medium. These cells were designated WC-1 14.07. Next, cell stocks of WC-1 14.07 were prepared. WC-1 14.07 cells were frozen in 90% fetal bovine serum and 10% DMSO and stored in the vapor phase of liquid nitrogen.

Example 2

Phenotypic Analysis of WC-1 14.07.

On about day 120, initial phenotype analysis was performed to determine whether WC-1 14.07 cells were derived from dendritic cells (DC) or macrophages. Phenotypic analysis of WC-1 14.07 cells was performed by flow cytometry. WC-1 14.07 cells were incubated with monoclonal antibodies to CD11c, CD80, CD86, CD83, CD40 and HLA-DR, -DP, -DQ (all purchased from Pharmingen, San Diego, Calif.). These monoclonal antibodies were directly conjugated to the fluorochromes fluorescein isothiocyanate (FITC) or phycoerythirn (PE), which fluoresce when excited at certain wavelengths. WC-1 14.07 cells were also incubated with monoclonal antibodies to hgp100 (HMB45, Accurate Chemical Westbury, N.Y.) and s100 (Chemicon Temecula, Calif.). WC-1 14.07 cells stained with monoclonal antibodies were analyzed on a FACScan flow cyotmeter (Becton Dickinson, San Jose Calif.) equipped with an argon ion laser at 488 nm excitation wavelength. Fluorescence is proportional to the amount of fluorochrome bound to the WC-1 14.07 via the monoclonal antibody. WC-1 14.07 cells were also stained with appropriate PE-conjugated or FITC-conjugated isotypic antibody controls to quantitate nonspecific binding. Nonspecific binding was subtracted from specific binding during analysis. WC-1 14.07 cells stained with monoclonal antibodies to hgp100 and s100.

Flow cytometry revealed that the WC-1 14.07 cells were CD11c−, CD80−, CD86− and CD40−; the cells were CD14+ and HLA-A2+. Based on the flow cytometry results it was concluded that WC-1 14.07 is not of DC origin. Phenotypic analysis was repeated at or around day 150. WC-1 14.07 were still CD11c, CD80 and CD86 negative, weakly CD14+, HLA-DR, -DQ, -DP negative and were not recognized by an anti-human fibroblast antibody. WC-1 14.07 cells reacted with antibody to s100, a marker of melanocyte differentiation. This observation, together with cell morphology and macroscopic evidence of melanin production, indicates that WC-1 14.07 is of melanocyte origin. WC-1 14.07 was also screened for hgp100 production by staining with a monoclonal antibody to human hgp100 (HMB45). HMB45 is a mouse monoclonal IgG1, kappa from Accurate Chemical and Scientific Corporation in Westbury N.Y. WC-1 14.07 was determined to express internally moderate amounts of hgp100.

Example 3

Analysis of WC-1 14.07 Surface Markers

WC-1 14.07 cells were harvested by Trypsin-EDTA and washed one time in PBS containing 0.1% bovine serum albumin (BSA). Approximately $5 \times 10^5$ cells were aliquoted in 15 cc conical centrifuge tubes. Live cells were incubated with fluorescein isothiocyanate (FITC) or phycoerythrin (PE) conjugated monoclonal antibodies to anti-CD11c, anti-CD80, anti-CD86, anti-CD40, anti-CD14, anti-HLA-DR and -DQ or anti-HLA A2 for 50 minutes on ice in the dark. Following the incubation, cells were washed two times with PBS containing 0.1% BSA. Cell pellets were resuspended in PBS and analyzed by flow cytometry.

Example 4

Analysis of WC-1 14.07 Internal Markers

Internal expression of s100, hgp100 and 5B5 (Dako Corporation Carpinteria Calif.), a fibroblast marker, was done using Pharmingens' internal expression kit which uses saponin and paraformaldehyde to permeabilize and fix the cells. Cells were incubated with the purified mouse monoclonal antibody for 50 minutes on ice in the dark followed by two washes in PBS containing 0.1% BSA. Cells were further incubated with FITC conjugated goat anti-mouse immunoglobulin for 30 minutes on ice. Cells were washed two times, resuspended in PBS and analyzed by flow cytometry.

Example 5

Cloning of WC-1 14.07

WC-1 14.07 was cloned by limiting dilution where 0.3 cells were added/well in the presence of 800 units/ml of GM-CSF. Clones were screened by flow cytometry to identify those expressing high levels of hgp100. One such clone, designated clone 14, was identified as the highest expresser of hgp100. Clone 14 was cloned again, passaged 17 times in growth medium without GM-CSF, and designated WC-1 14.07.

This cell line was deposited in accordance with the Budapest Treaty with the American Type Culture Collection (ATCC), 10801 University Blvd, Manassas, Va. 20110, an accepted Depository Authority, on Feb. 3, 2000 and given the designation ATCC PTA-1275.

Example 6

Characterization of WC-1 14.07

MHC Class I expression was examined. WC-1 14.07 cells were found to be negative for MHC Class I. PCR analysis confirmed loss of Class I MHC determinants. Primers for exon 2 and 3 were obtained from Visual Diagnostics, the sequences of which are proprietary. PCR amplification using these primers was done but resulted in no amplification of the expected sequence.

Example 7

Transfection with MHC Determinants.

WC-1 14.07 cells are first transfected with a DNA plasmid expressing HLA-A 0201 such as pcDNA3-HLA-A2.1.1 (Kawakami Y et al. Proc Natl. Acad. Sci 91: 6458–6462, 1994), with a transfection reagent such as DMRIE C (Gibco, Grand Island NY) for 1 hour at 37°. After transfection, the cells are washed and cultured for an additional 24 hours. Expression analysis is then performed using a monoclonal antibody to HLA A2 obtained from One Lambda Inc. (Canoga Park Calif.). After demonstrating surface expression of HLA A2, transfected WC-1 14.07 cells are labeled with $^{51}$Cr and used as targets in a cytotoxicity assay. Alternatively, WC-1 14.07 is incubated with T cell effectors and the release of interferon-gamma by the T cells quantitated by ELISPOT.

We claim:

1. The adherent melanocyte cell line WC-1 14.07 (ATCC PTA-1275).

2. A modified cell line comprising the cell line of claim 1 transfected with one or more nucleic acid sequences encoding an Class I MHC molecule.

3. The cell line of claim 2, wherein the Class I MHC molecule is expressed on the surface of said cell line.

4. The cell line of claim 3, wherein said Class I MHC molecule is HLA A 0201.

5. A composition comprising cells of the adherent melanocyte cell line WC-1 14.07 (ATCC PTA 1275).

6. A composition comprising cells of claim 1 transfected with at least one nucleic acid sequence encoding an Class I MHC molecule.

7. The composition of claim 6, wherein the Class I MHC molecule is expressed on the surface of the cell.

8. The composition of claim 6 or 7 wherein the Class I MHC molecule is HLA A 0201.

* * * * *